(12) United States Patent
Sakamoto et al.

(10) Patent No.: US 7,418,109 B2
(45) Date of Patent: Aug. 26, 2008

(54) DIAPHRAGM STRUCTURE OF LIGHT SOUND CONVERTER

(75) Inventors: Yoshio Sakamoto, Hachiouji (JP); Takahiro Imai, Kawasaki (JP)

(73) Assignee: Kabushiki Kaisha Kenwood, Tokyo (JP)

( * ) Notice: Subject to any disclaimer, the term of this patent is extended or adjusted under 35 U.S.C. 154(b) by 709 days.

(21) Appl. No.: 10/479,846

(22) PCT Filed: Jun. 13, 2002

(86) PCT No.: PCT/JP02/05893

§ 371 (c)(1),
(2), (4) Date: Dec. 8, 2003

(87) PCT Pub. No.: WO02/104069

PCT Pub. Date: Dec. 27, 2002

(65) Prior Publication Data

US 2004/0238267 A1   Dec. 2, 2004

(30) Foreign Application Priority Data

Jun. 19, 2001 (JP) .............................. 2001-184530

(51) Int. Cl.
*H04R 1/00* (2006.01)
*H04R 9/06* (2006.01)
*H04R 11/02* (2006.01)
*G10K 13/00* (2006.01)

(52) U.S. Cl. ...................... 381/423; 381/184; 381/395; 381/424; 381/429; 181/161; 181/167

(58) Field of Classification Search .................. 381/342, 381/347, 388, 395, 189, 398, 423, 424, 426, 381/427, 429, 430, 433; 181/154, 155, 163, 181/164, 165, 167, 168, 170, 173, 174, 191
See application file for complete search history.

(56) References Cited

U.S. PATENT DOCUMENTS 1,707,658 A   4/1929   Elenschneider (Continued)

FOREIGN PATENT DOCUMENTS

EP   1 091 616   4/2001

(Continued)

OTHER PUBLICATIONS

International Search Report.

(Continued)

*Primary Examiner*—Wayne Young
*Assistant Examiner*—Dionne H Pendleton
(74) *Attorney, Agent, or Firm*—Eric J. Robinson; Robinson Intellectual Property Law Office, P.C.

(57) ABSTRACT

A diaphragm (1) of a light sound converter which has a high performance, is suitable for mass-production and has a slit (1s) formed therein. A light emitting element and a light receiving element are disposed at positions opposed to a reflective part (1a) of the diaphragm (1) having a pressure receiving surface part (1d) and the reflective part (1a), and light is radiated from the light emitting element to the reflective part (1a) of the diaphragm (1) and the reflected light from the reflective part (1a) is received by the light receiving element, whereby the position of the diaphragm (1) can be detected.

12 Claims, 11 Drawing Sheets

U.S. PATENT DOCUMENTS 1,997,790 A 4/1935 Heidrich
5,854,846 A * 12/1998 Beavers .................. 381/174

FOREIGN PATENT DOCUMENTS

| GB | 2 055 528 | 3/1981 |
| --- | --- | --- |
| JP | 59-025895 | 2/1984 |
| JP | 60-123197 | 7/1985 |
| JP | 01-168199 | 7/1989 |
| JP | 06-125599 | 5/1994 |
| JP | 08-096677 | 4/1996 |
| JP | 11-153454 | 6/1999 |
| JP | 2001-028796 | 1/2001 |
| JP | 2002-159095 | 5/2002 |
| WO | 01/028286 | 4/2001 |

OTHER PUBLICATIONS

Examiner Office Action dated Aug. 22, 2006 for Application No. JP 2001-184530.
Supplementary European Search Report (Application No. 02738682.0) Dated May 28, 2008.

* cited by examiner

PRIOR ART

FIG.6

PRIOR ART

FIG. 7

PRIOR ART

FIG. 8

PRIOR ART

FIG. 9

PRIOR ART

FIG. 10

PRIOR ART

FIG.11

PRIOR ART

DIAPHRAGM STRUCTURE OF LIGHT SOUND CONVERTER

TECHNICAL FIELD

The present invention relates to an acoustic-electric converter for converting a vibrational displacement of a diaphragm caused by sounds into an electric signal by utilizing a change in light radiated to the diaphragm, and more particularly to improvements on the structure of a diaphragm of the acoustic-electric converter.

RELATED BACKGROUND ART

With reference to FIGS. 5 to 11, description will be made on examples of a conventional acoustic-electric converter (hereinafter called a light sound converter) for converting a vibrational displacement of a diaphragm caused by sounds into an electric signal by utilizing a change in light caused by the vibrational displacement. A diaphragm 7 of a light sound converter shown in FIG. 5 has a flat film made of an aluminum foil or the like having a thickness of, for example, about 2 μm, without performing molding, working and the like.

Figure 5:
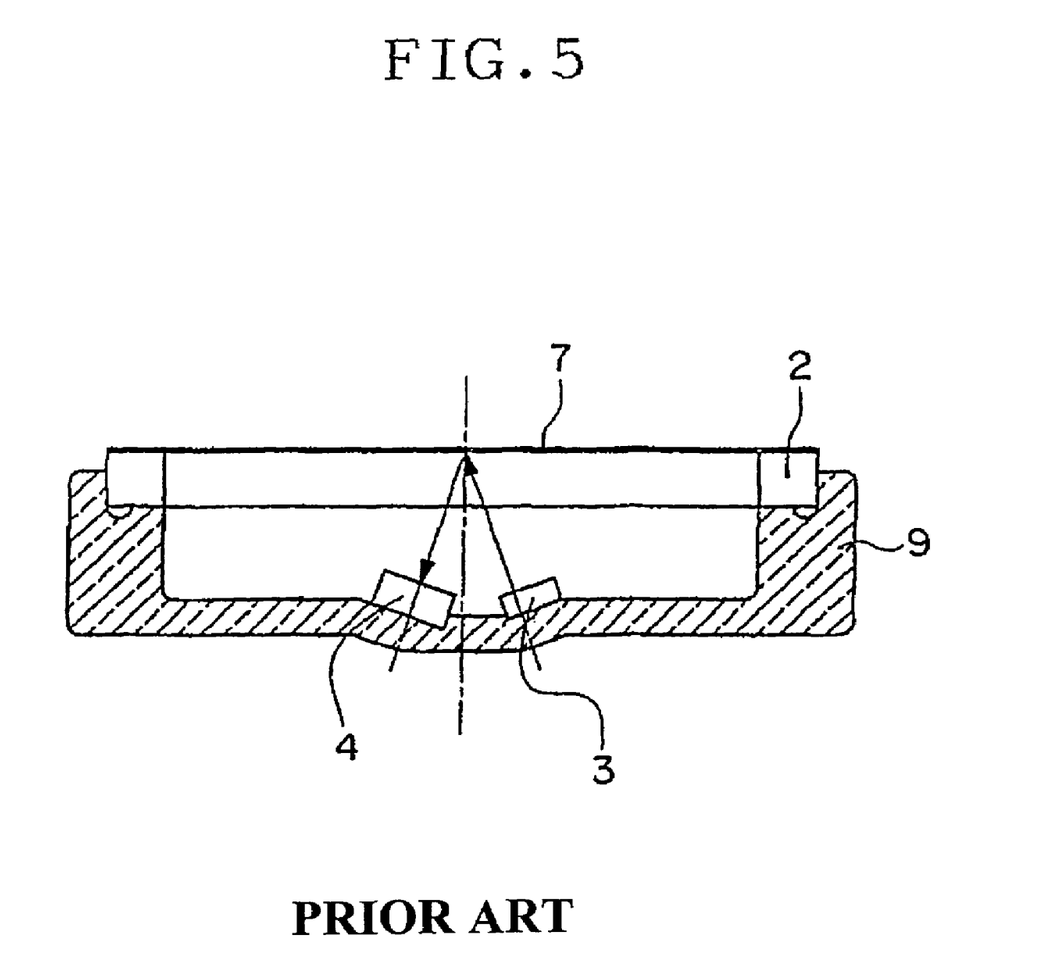
FIG. 5 is a cross sectional view showing an example of a conventional light sound converter.

Light emitted from a light emitting element 3 is reflected at the surface of a planar diaphragm 7 and received by a light receiving element 4. In order to prevent reflected light from being disturbed, it is necessary to eliminate crinkling, sagging and the like and maintain flatness of the diaphragm 7 made of a very thin film. To this end, the diaphragm 7 of a planar film is formed by applying a predetermined tension to the diaphragm 7 to eliminate crinkling, sagging and the like.

While the thin film of the diaphragm is stretched, a ring 2 is adhered to an outer peripheral area of the diaphragm by means of adhesive or the like. Therefore, the thin film constituting the diaphragm is maintained flat by a predetermined tension and the outer peripheral area of the diaphragm is fixed to the ring 2. The ring 2 is fixed to a frame 9 which supports a light emitting element 3 and a light receiving element 4. A laser beam radiated from the light emitting element 3 and reflected at the diaphragm 7 is received by the light receiving element 4 to detect a displacement of the diaphragm 7 from an output of the light receiving element 4.

Since tension is applied to this conventional planar diaphragm 7, there arises a problem of a small compliance of the diaphragm 7. The diaphragm 7 is therefore harder than usual. A vibration amplitude of the diaphragm 7 therefore becomes smaller than usual, i.e., the vibration amplitude from which a wide range of frequencies is to be detected becomes smaller than usual.

To solve this problem, another method of forming a diaphragm has been proposed. According this method, a metal thin film is vapor-deposited to a thickness of, for example, about 1 μm on a surface of a wafer or the like. A ring is adhered to the metal thin film or foil formed on the wafer surface, and the ring together with the adhered metal thin film is removed from the wafer to obtain the diaphragm. Even with this method, it has been found that a weak tension is applied to the diaphragm because adhesive on the adhesive surfaces, particularly adhesive reaching to the inner peripheral area of the ring, shrinks when it is hardened.

Generally, the frequency characteristics of a planar diaphragm are not flat and the diaphragm resonates at its specific frequency to generate a peak. It is well known that the vibration amplitude of the diaphragm becomes small at the frequency other than the resonance frequency. It is difficult to obtain a vibration amplitude sufficient for detecting a wide range of frequencies, resulting in a narrow reproduction band of the light sound converter for detecting a vibration of the diaphragm by utilizing light.

Figure 6:
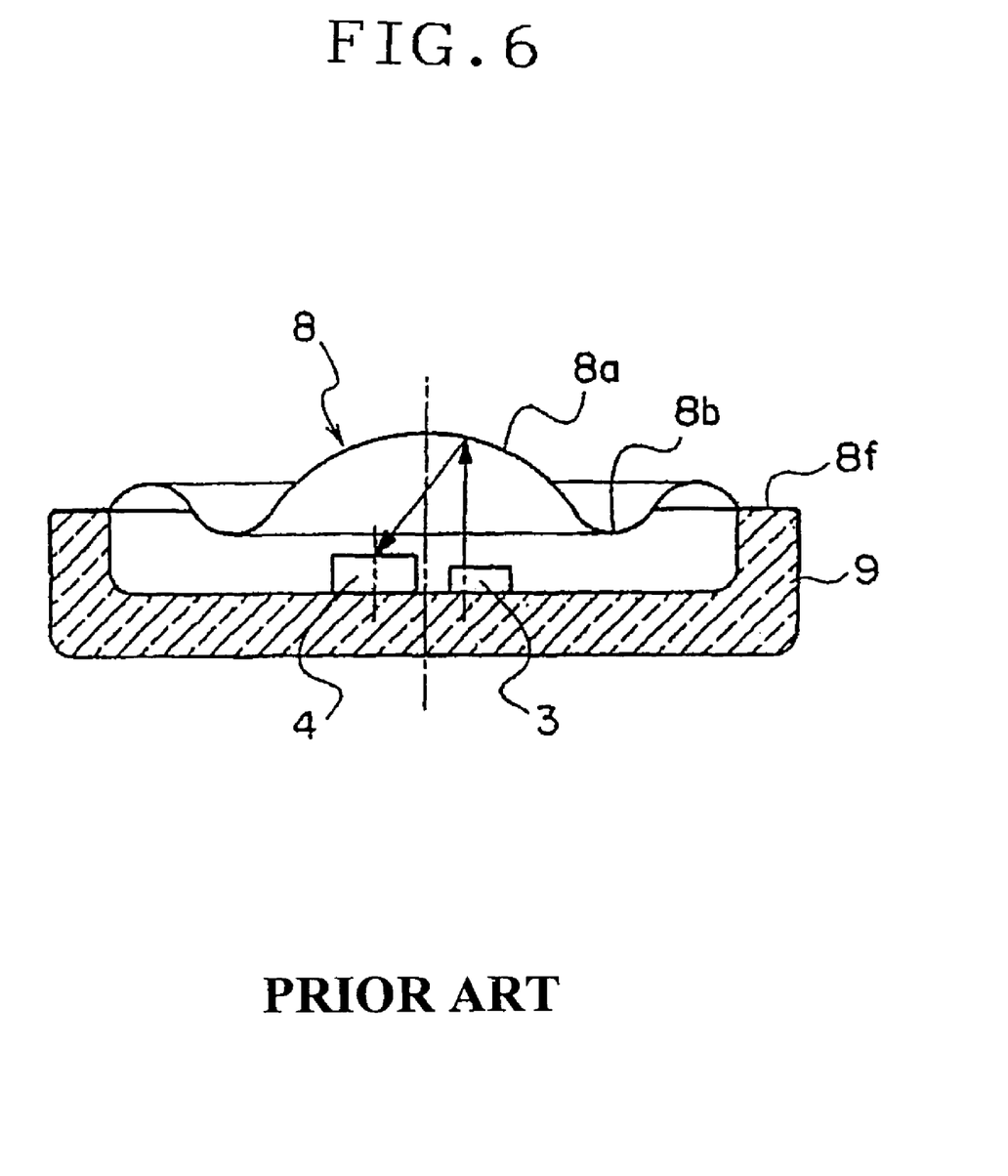
FIG. 6 is a cross sectional view showing another example of a conventional light sound converter.

To overcome this disadvantage, the present applicant has already proposed a method illustrated in FIG. 6. According to this proposal, a reflective part 8a of a diaphragm 8 has a dome shape, a suspension part 8b is formed continuously with an outer peripheral area of the reflective part 8a, and an adhesion margin part 8f is integrally formed with an outer area of the suspension part 8b. This adhesion margin part 8f is adhered to a frame 9. A laser beam radiated from a light emitting element 3 fixed to the frame 9 shown in FIG. 6 and reflected at the reflective part 8a is received by a light receiving element 4 fixed to the frame 9 to detect a displacement of the reflective part 8a from an output of the light receiving element 4.

Figure 7:
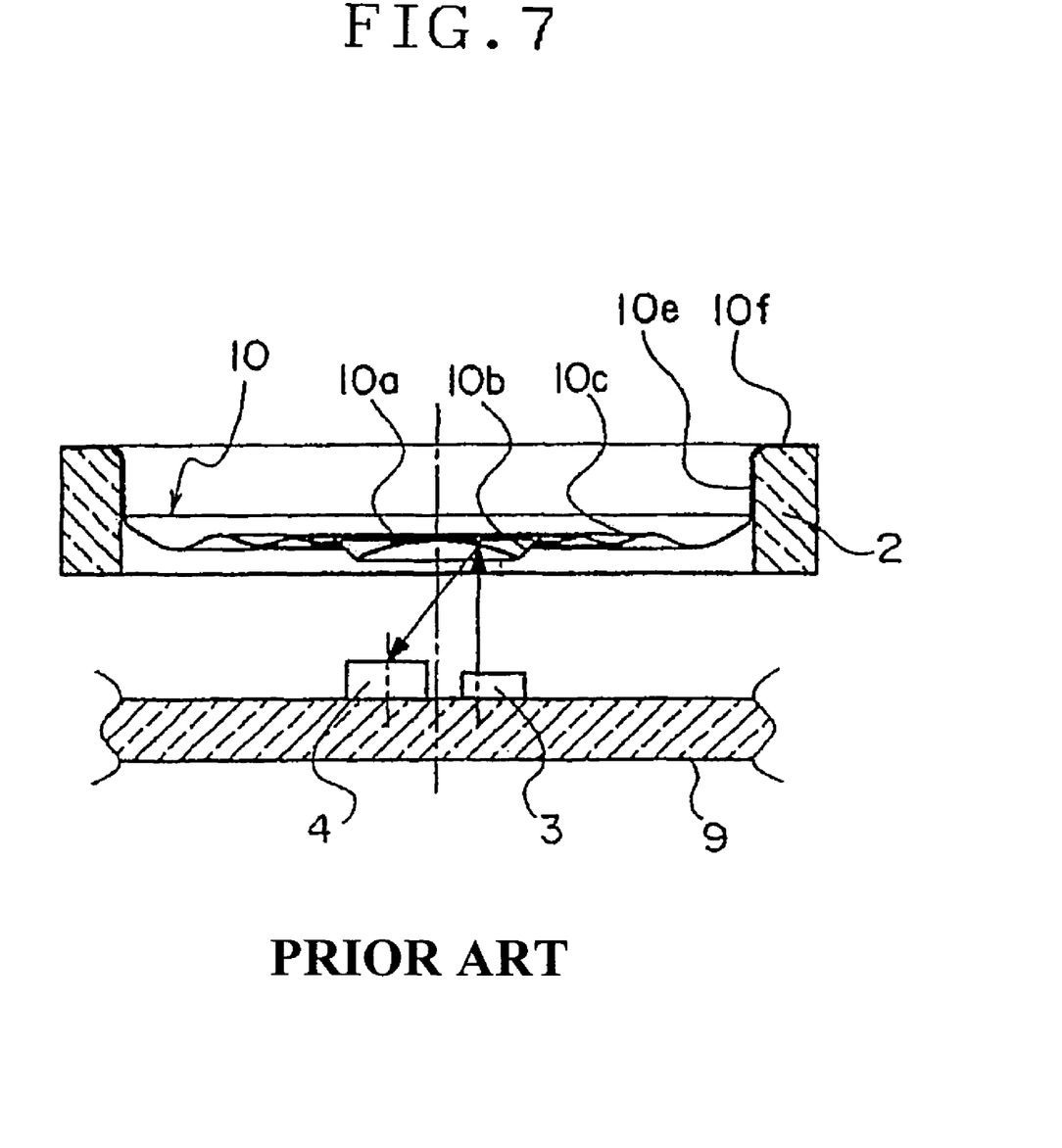
FIG. 7 is a cross sectional view showing still another example of a conventional light sound converter.
Figure 8:
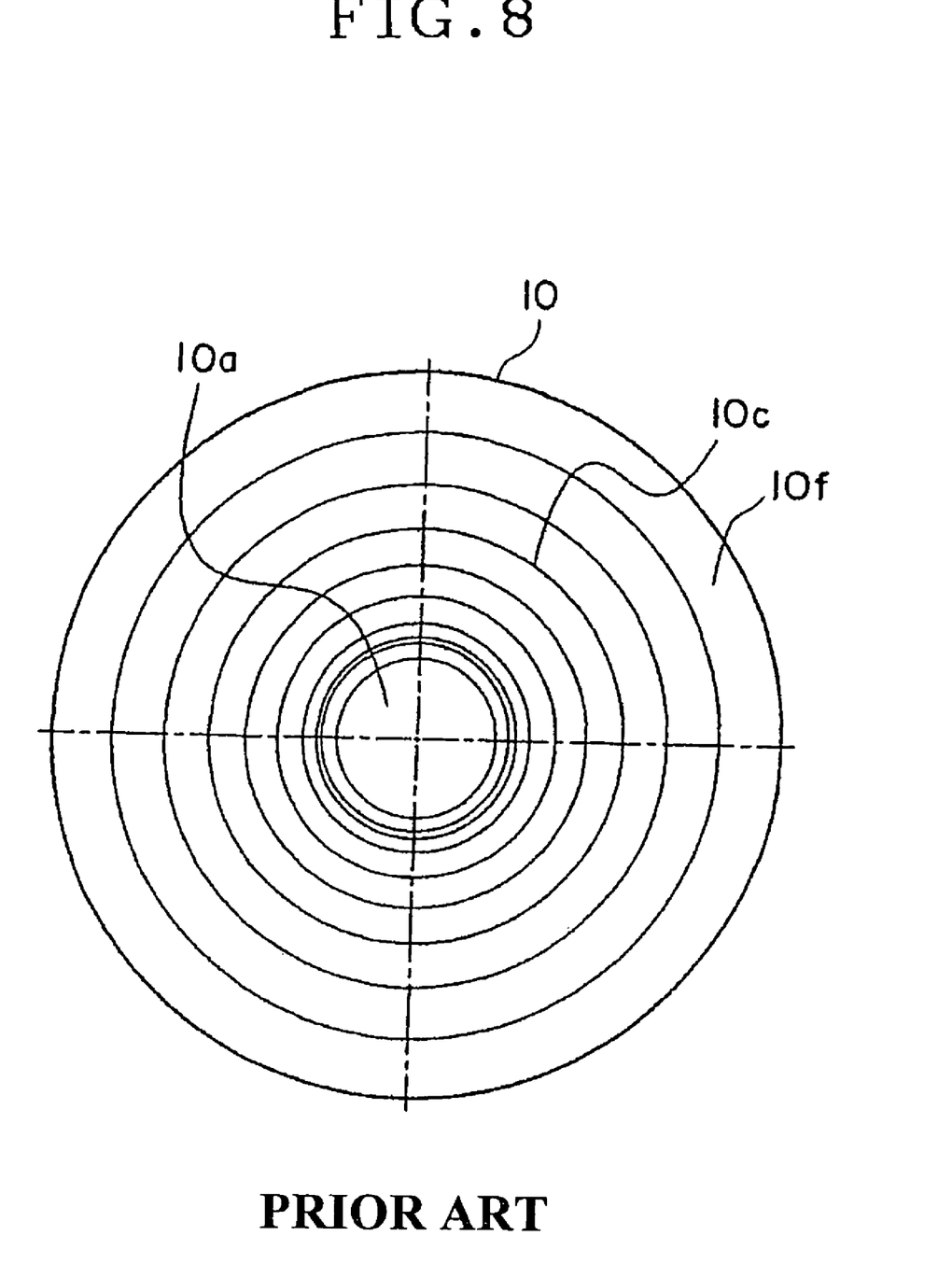
FIG. 8 is a plan view of the diaphragm of the light sound converter shown in FIG. 7.
Figure 9:
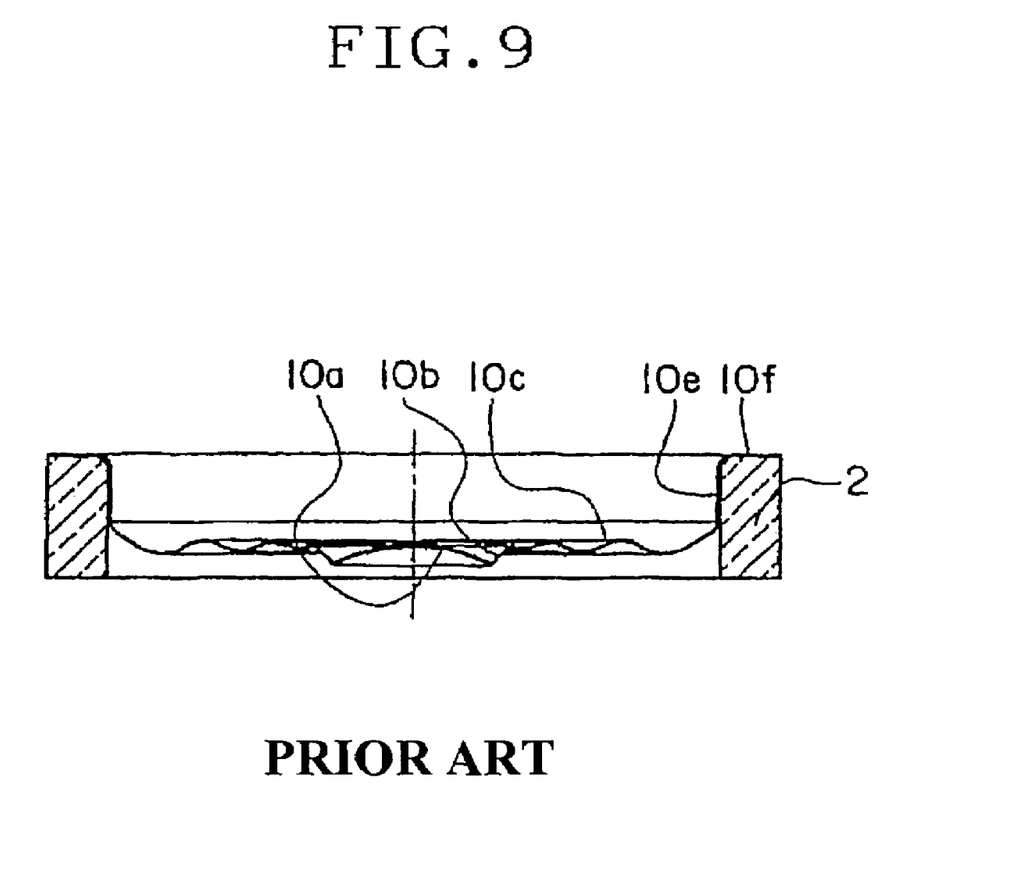
FIG. 9 is a cross sectional view of the diaphragm of the light sound converter shown in FIG. 7.

This proposal also refers to a diaphragm 10 which has a large area suspension part 10c as shown in FIGS. 7 to 9 in order to obtain a higher vibration amplitude. A reflective part 10a of a dome shape is disposed in the central area of the diaphragm 10. A laser beam radiated from a light emitting element 3 fixed to a frame 9 and reflected at the reflective part 10a is received by a light receiving element 4 fixed to the frame 9 to detect a displacement of the reflective part 10a from an output of the light receiving element 4.

A rising part 10b rising obliquely at 45° is continuously formed with an outer peripheral area of the dome-shaped reflective part 10a. The suspension part 10c is formed integrally with the outer peripheral area of the rising part 10b, and constituted of five concentrical corrugations extending radially and each defined by a curve having a predetermined radius.

A vertical rising part 10e is formed continuously with the outer peripheral area of the suspension part 10c, and an adhesion margin part 10f is integrally formed with and horizontally protruded from the outer periphery of the rising part 10e. This adhesion margin part 10f is adhered to a ring 2. Although not shown, the ring 2 is formed integrally with the frame 9.

As well known, recent requirements of making compact a light sound converter are very severe. In order to meet this compactness requirements, the diameter of a diaphragm with a dome-shaped reflective part, a corrugation type suspension part and the like is required to be short. A compliance of the diaphragm becomes inevitably small.

The experiments made by the present inventors have verified that as the same sound pressure is applied to a diaphragm, the vibration amplitude becomes small in inverse proportion with the square of the area of the diaphragm. As the vibration amplitude of the diaphragm becomes low, it is obviously difficult, for the light sound converter for detecting a vibration displacement of the diaphragm by utilizing light, to correctly detect the vibration amplitude.

As a method capable of overcoming this disadvantage, it is easily conceivable to thin the base material of a diaphragm having a dome shape integrally formed with the reflective part 10a, suspension part 10c and the like. For example, a metal foil or resin film having a thickness of 4 μm is replaced by a metal foil or resin film having a thickness or 3 μm or thinner.

With this approach, however, although it is effective to improve the compliance of the suspension part 10c, the dome shape reflective part 10a becomes more likely to resonate as the base material is made thin. Namely, since the diaphragm is thin, a number of split resonances occur in the reproduction vibration frequency band. This approach is therefore associated with the disadvantage that there is a large strain in the reproduction band and the sound quality is degraded very much.

It is well known that the thinner a metal foil, a film or the like of the base material of a diaphragm is made, the vibration amplitude of the diaphragm becomes higher. The experiments made by the present inventors have confirmed that a thinning rate of a diaphragm is smaller than a raising rate of a vibration amplitude of the diaphragm. It is also well known that as a film is made thinner, a mechanical strength weakens which is necessary for maintaining the original structure of the film. Very delicate works of handling such a film during manufacture are therefore required and the productivity is degraded.

In order to obtain a higher vibration amplitude of a diaphragm having a predetermined area and made of a base material providing a strength eliminating resonance during vibration, it is desired to increase the compliance of only the suspension part so as to allow the reflective part to easily vibrate, i.e., it is desired to provide the suspension part with a high elasticity.

A general approach to improving the compliance of a suspension part of a diaphragm made of a film already exists. According to this approach, the area of the suspension part is reduced to provide the suspension part with a high elasticity.

Figure 10:
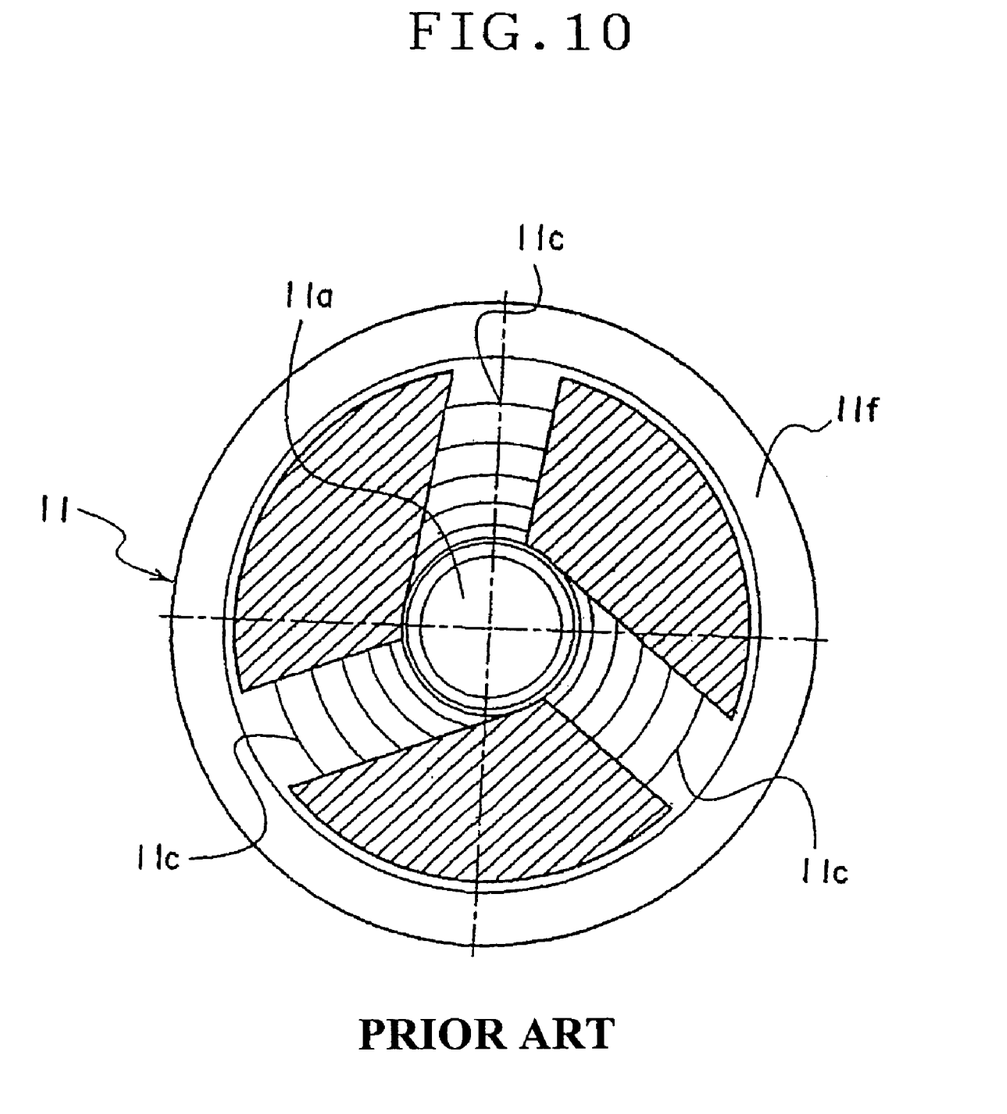
FIG. 10 is a plan view showing still another example of a diaphragm of a conventional light sound converter.
Figure 11:
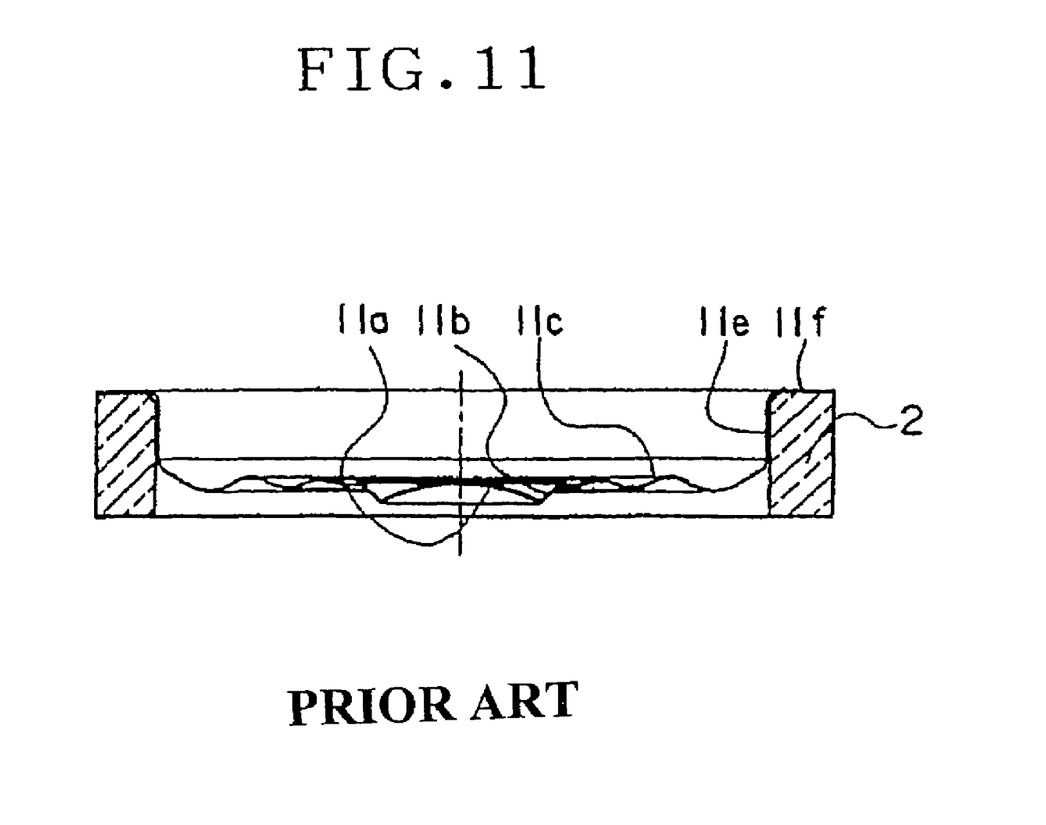
FIG. 11 is a cross sectional view of the diaphragm shown in FIG. 10.

For example, the suspension part is made narrow like a cantilever which supports the reflective part of the diaphragm. The present inventors have formed a cantilever suspension part 11c on a diaphragm 11 which is partially removed as shown in FIGS. 10 and 11, i.e., the diaphragm with its hatched portions being removed.

Description will be made on the shape of the diaphragm 11 before removing the hatched portions. A rising part 11b rising obliquely at 45° is continuously formed with an outer peripheral area of a dome-shaped reflective part 11a. The suspension part 11c is formed integrally with the outer peripheral area of the rising part 11b, and constituted of five concentrical corrugations extending radially and each defined by a curve having a predetermined radius.

A vertical rising part 11e is formed continuously with the outer peripheral area of the suspension part 11c, and an adhesion margin part 11f is integrally formed with and horizontally protruded from the outer periphery of the rising part 11e. This adhesion margin part 10f is adhered to a ring 2. The cantilever suspension part 11c formed in this manner had most of the area around the dome shape reflective part 11a of the diaphragm 11 being removed as shown in FIG. 10. The cantilever suspension part 11c also had a large width.

The reason for this is ascribed to the shapes of trimming molds determined by taking into consideration the productivity of partially removing the diaphragm through press trimming. More specifically, in order to retain the strength of trimming molds, a punch and a die, it is required that the punch and die have allowable minimum widths. This restriction of the minimum widths results in the limited shape of the cantilever suspension part 11c. The shape of the cantilever suspension part 11c is therefore limited by a press trimming method currently used in most common.

Measurements were conducted for a vibration amplitude of the diaphragm 11 having the cantilever suspension part 11c and for a vibration amplitude of a diaphragm before partial removal of the diaphragm by trimming molds. For the measurements, the adhesion margin part of the diaphragm was clamped with a diaphragm mounting jig having a predetermined ring shape. The diaphragm mounted on the jig was placed in front of a speaker to vibrate the diaphragm. A sound pressure of 94 dB at a frequency of 1 KHz was applied to the diaphragm from the speaker. The vibration amplitude of the diaphragm vibrated in this state was measured by a laser doppler method.

The measurement results indicated that the diaphragm with the cantilever suspension part 11c had a vibration amplitude slightly higher than that of the diaphragm without the cantilever suspension part. In terms of numerical values, the diaphragm without the cantilever suspension part had an amplitude of 0.076 µm to 0.1µm, whereas the diaphragm with the cantilever suspension part 11c had an amplitude of 0.08 µm to 0.12 µm. This difference is small, verifying that the effects of the cantilever part are less.

DISCLOSURE OF THE INVENTION

It is an object of the present invention to solve the above-described problems of the diaphragm of a conventional light sound converter, to improve the diaphragm structure proposed by the present applicant, and to provide a diaphragm of a light sound converter having a high performance and being suitable for mass-production.

In order to solve the problems, the present inventors have paid attention not only to the shape of a cantilever suspension part but also to the pressure receiving surface area of the diaphragm to determine the shape of the cantilever suspension part. In order to efficiently receive vibrations of air, obviously it is preferable that the pressure receiving surface area of the diaphragm is large.

If the cantilever suspension part 11c is formed on the diaphragm 11 by a conventional press trimming method, most of the diaphragm 11 excepting the reflective part 11a is required to be removed. As the diameter of the diaphragm 11 becomes smaller, the removal ratio becomes larger.

The conventional diaphragm structure receives a sound pressure, i.e., a pressure caused by air wave of expansion with almost only the reflective part 11a. The peripheral area of the reflective part 11a can be said almost a free space. It is inevitable that the pressure receiving area for receiving air pressure becomes small. The air pressure driving the reflective part 11a causes air to move around the reflective part 11a, so that the vibration amplitude of the reflective part 11a may be hindered.

According to the invention, a diaphragm made of a thin film, particularly a diaphragm having a small diameter, is formed by integrally molding a reflective part of a dome shape, suspension parts formed at the outer periphery of the reflective part, an adhesion margin part and the like. Slits having a width as narrow as possible (0.3 mm or narrower, preferably 0.1 mm or narrower) are formed in desired areas of the diaphragm. Each slit defines an outer periphery of a cantilever suspension part and an outer periphery of the pressure receiving surface part of the diaphragm.

EMBODIMENTS OF THE INVENTION

Embodiments of the invention will be described in detail. FIGS. 1 to 4 show examples of the structure of a diaphragm of a light sound converter according to the embodiments of the invention. In the embodiments, each diaphragm was formed by thermally molding a resin film having a thickness of about 9 μm to about 16 μm.

Figure 1:
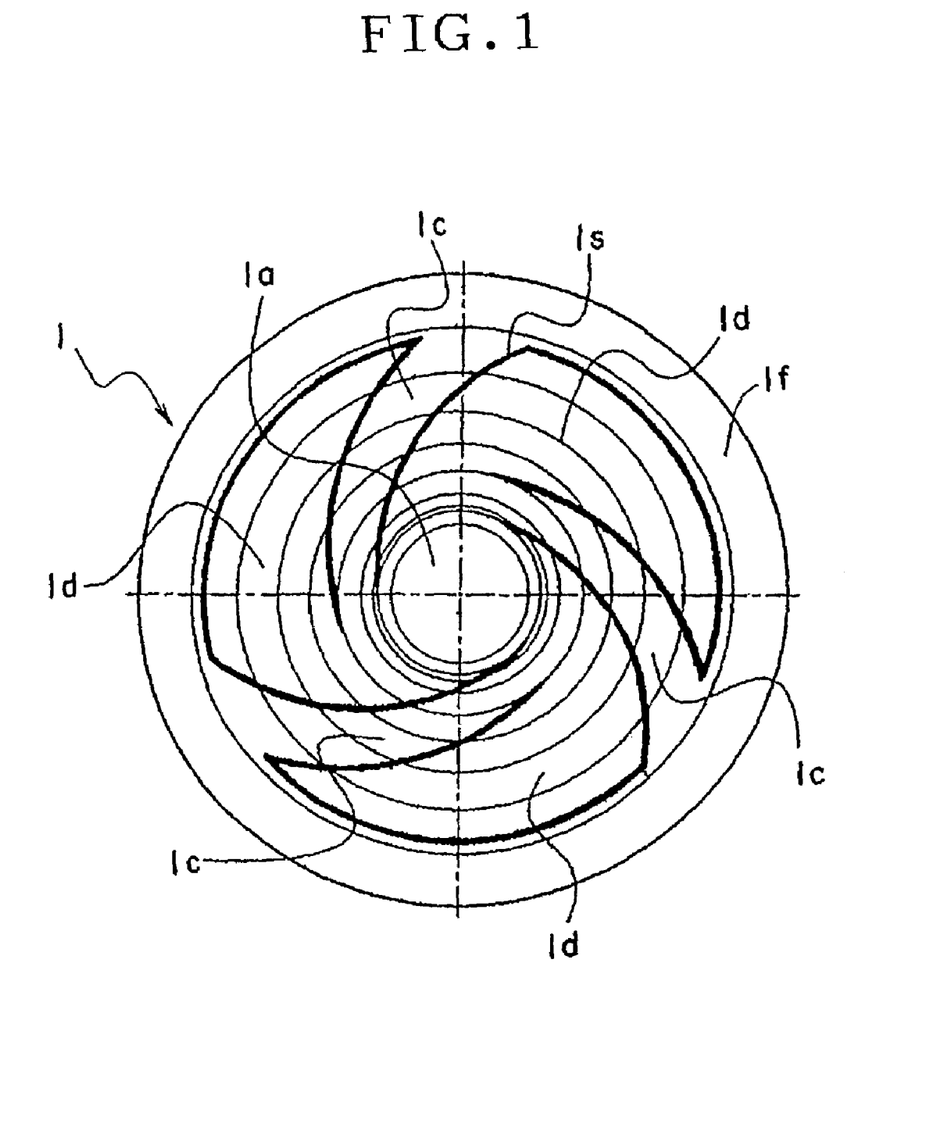
FIG. 1 is a plan view showing a diaphragm of a light sound converter according to a first embodiment of the invention.
Figure 2:
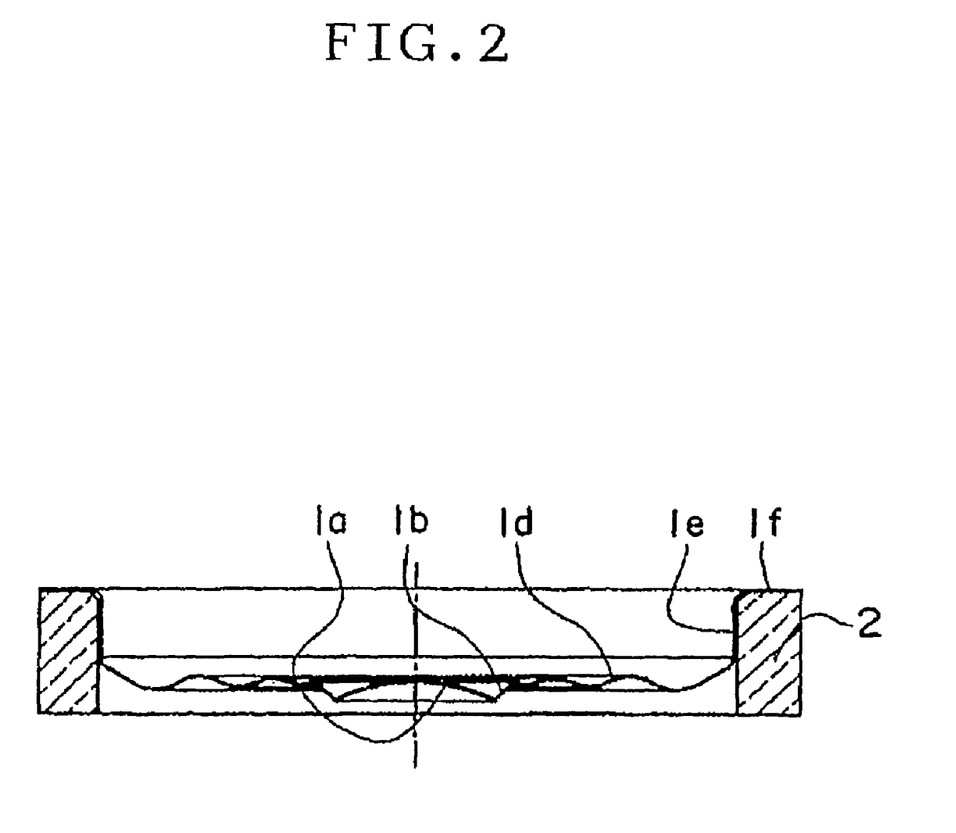
FIG. 2 is a cross sectional view of the diaphragm shown in FIG. 1.

FIGS. 1 and 2 show the first embodiment of the invention. The fundamental shape of a diaphragm before slits $1s$ indicated by bold solid lines in FIG. 1 are formed is similar to that of the conventional diaphragm shown in FIGS. 7 to 9 before partial removal of the diaphragm by trimming molds. Referring to FIGS. 1 and 2, a dome shape reflective part $1a$ is formed in the central area of a diaphragm 1. The reflective part $1a$ has a diameter of 1.3 mm and a radius of curvature of 1.5 mm. A rising part $1b$ rising obliquely at 45° is formed continuously with an outer peripheral area of the reflective part $1a$. A suspension part $1c$, $1d$ is formed integrally with the outer peripheral area of the rising part $1b$, and constituted of five concentrical corrugations extending radially and each defined by a curve having a predetermined radius.

A vertical rising part $1e$ is formed continuously with the outer peripheral area of the suspension part $1c$, $1d$ and an adhesion margin part $1f$ is integrally molded and horizontally protrudes by about 0.5 mm from the outer periphery of the rising part $1e$ having a height of 0.6 mm. A metal film of nickel, aluminum or the like is vapor-deposited on the inner surface of the dome shape reflective part $1a$ to provide a laser beam reflection surface.

As shown in the plan view of FIG. 1, the slits $1s$ of the diaphragm are formed by applying a laser beam along patterns indicated by bold solid lines. The slit $1s$ has a width of about 45 μm. The pattern of the slit includes an arc (hereinafter called an arc A) having a radius of 2.204 mm and extending outward along a tangential direction from a point on the outermost periphery (a circle having a radius of 0.95 mm) of the oblique rising part $1b$ formed continuously with the outer periphery of the circular reflective part $1a$. This arc A reaches a circle having a radius of 2.408 mm and being concentrical with the reflective part $1a$.

The pattern of the slit also includes an arc (hereinafter called an arc B) having a radius of 2.55 mm and extending outward along a tangential direction like the arc A from a point offset upward by 0.4 mm from the arc A. Similar to the arc A, the arc B reaches a circle having a radius of 2.408 mm and being concentrical with the reflective part $1a$. Three pairs of the arcs A and B are disposed at a pitch of 120° relative to the center of the reflective part. The pattern of the slit also includes an arc having a radius of 2.408 mm relative to the center of the diaphragm and formed between the distal end of the arc A of the first pair and the distal end of the arc B of the adjacent pair, between the distal end of the arc A of the second pair and the distal end of the arc B of the third pair, and between the distal end of the arc A of the third pair and the distal end of the arc B of the first pair. These arcs A and B and an arc therebetween constitute each pattern of the slit $1s$.

By forming the patterns having a predetermined width (45 μm) by laser trimming, arc cantilever suspension parts $1c$ are formed on the diaphragm, each cantilever suspension part having an inner mount width of 0.4 mm and an outer mount width of 1.08 mm and extending from the reflective part $1a$ toward an outer periphery of the diaphragm. In this embodiment, the outermost periphery of the diaphragm having a diameter of 3 mm is formed by laser trimming. After the laser trimming, the final diaphragm 1 can be obtained.

As an adhesion margin part $1f$ formed in the outermost peripheral area of the diaphragm is fixed to a ring or the like, pressure receiving surface parts $1d$ are defined which are constituted of the reflective part $1a$ and the areas of the corrugations other than the cantilever suspension parts $1c$. The pressure receiving surface parts $1d$ are disposed outside of the cantilever suspension parts $1c$ disposed in three areas at a pitch of 120° by laser trimming. The pressure receiving surface parts $1d$ are cut generally from the outermost periphery of the diaphragm 1.

The reflected part $1a$ and the pressure receiving surface parts $1d$ constituted of the reflective part $1a$ and the areas of the corrugations other than the suspension parts defined by the slits having a width of 45 μm, are therefore supported by the cantilever suspension parts $1c$. In this embodiment, slit trimming was performed by using excimer laser, YAG laser, carbon dioxide laser and the like. All of these laser beams were able to achieve the expected objectives.

Figure 3:
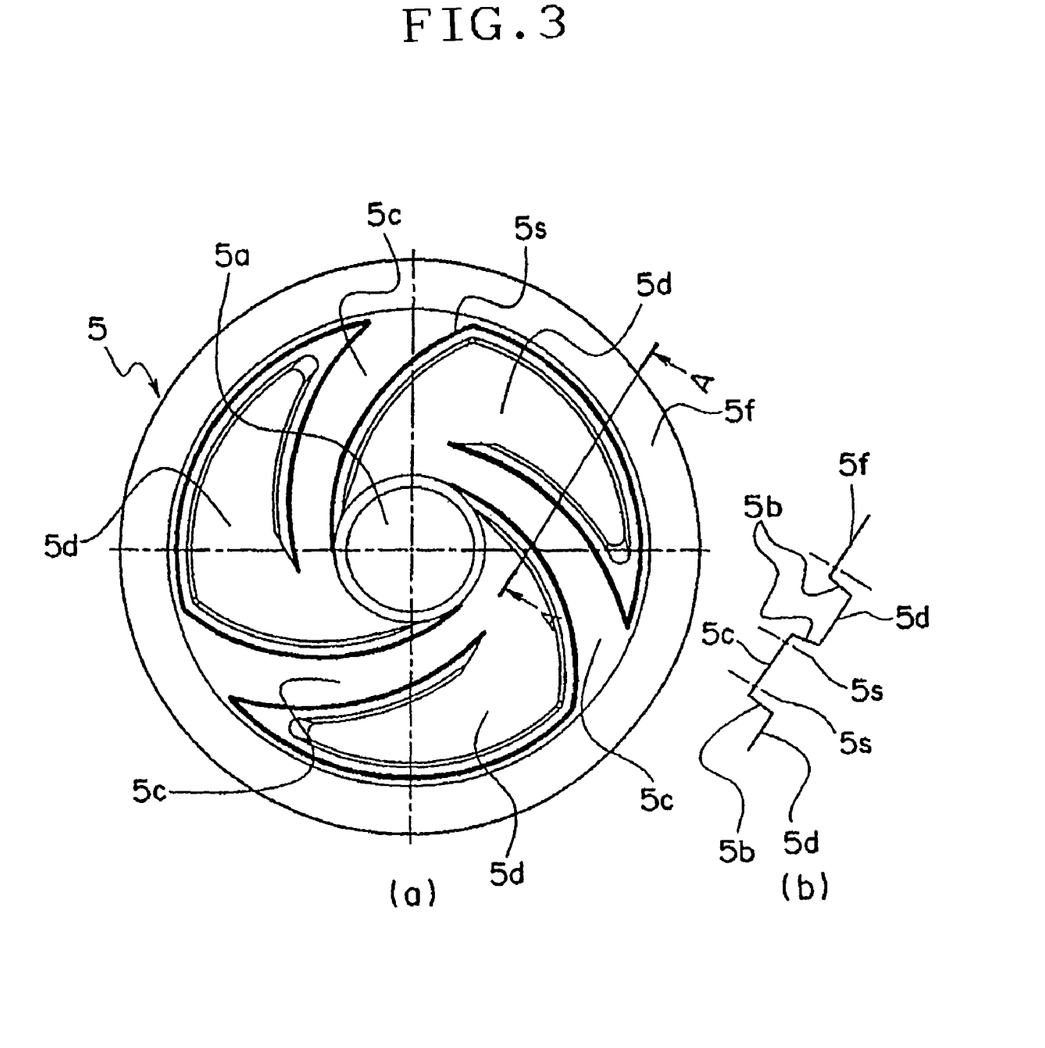
FIG. 3(a) is a plan view showing a diaphragm of a light sound converter according to a second embodiment of the invention.
FIG. 3(b) is a cross sectional view taken along line A-A shown in FIG. 3(a).

In the second embodiment shown in FIGS. 3(*a*) and 3(*b*), at the time of designing a diaphragm 5, the positions of cantilever suspension parts $5c$ for supporting a reflective part $5a$ are determined in advance. The height of each cantilever suspension part $5c$ is set different from the height of the nearby parts, and the pattern of each slit $5s$ is slightly changed from that of the first embodiment. As shown in a partial cross sectional view of FIG. 3(*b*), a rising part $5b$ can be formed at the whole outer periphery of a pressure receiving surface part $5d$.

Similar to the first embodiment, the cantilever suspension part $5c$ is continuous with an adhesion margin part $5f$ via a vertical rising part. For the purpose of drawing simplicity, corrugations are not drawn in FIG. 3(*a*).

Figure 4:
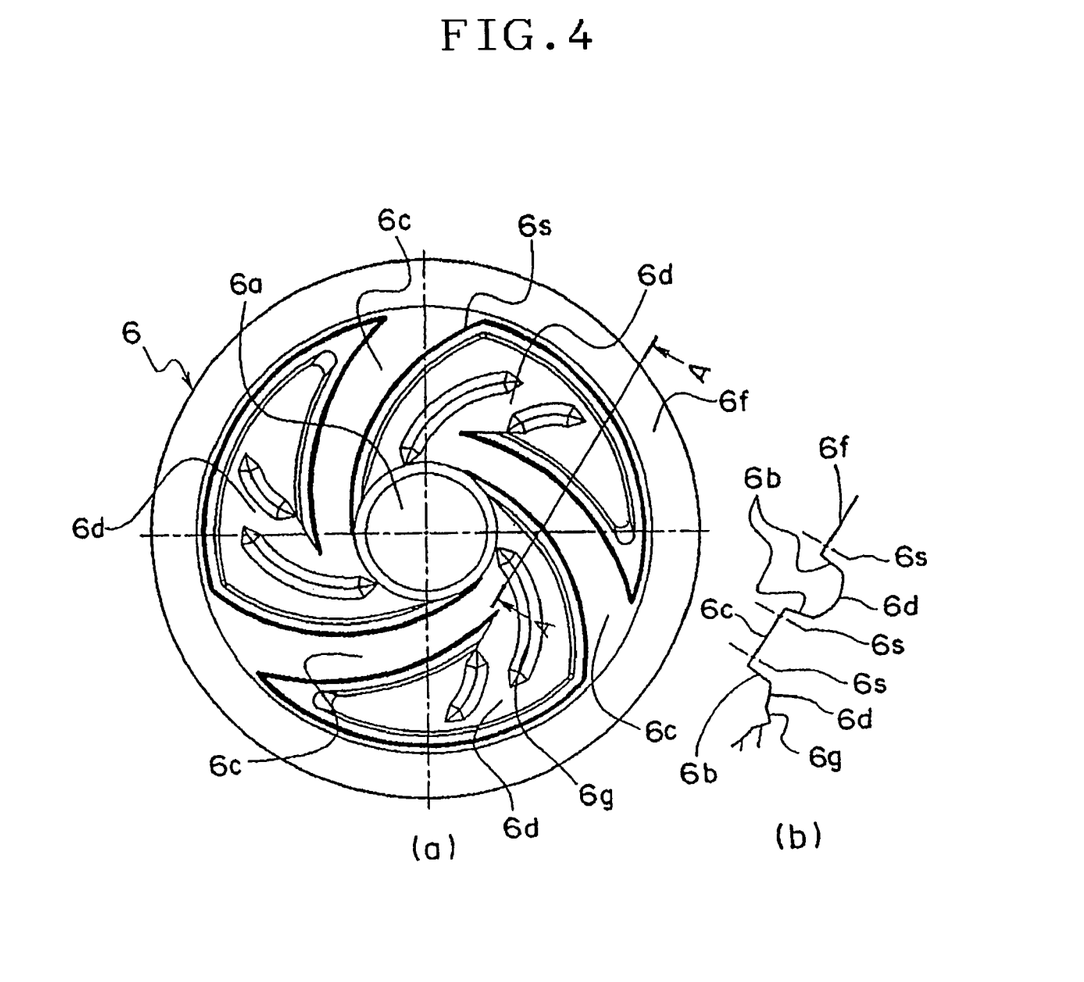
FIG. 4(a) is a plan view showing a diaphragm of a light sound converter according to a third embodiment of the invention.
FIG. 4(b) is a cross sectional view taken along line A-A shown in FIG. 4(a).

Similar to the second embodiment, in the third embodiment shown in FIGS. 4(*a*) and 4(*b*), the positions of cantilever suspension parts $6c$ for supporting a reflective part $6a$ of a diaphragm 6 are determined in advance. The height of each cantilever suspension part $6c$ is set different from the height of the nearby parts, and the pattern of each slit $6s$ is slightly changed from that of the first embodiment. As shown in a partial cross sectional view of FIG. 4(*b*), a rising part $6b$ can be formed at the whole outer periphery of a pressure receiving surface part $6d$.

Similar to the first embodiment, the cantilever suspension part $6c$ is continuous with an adhesion margin part $6f$ via a vertical rising part. For the purpose of drawing simplicity, corrugations are not drawn in FIG. 4(*a*).

It is apparent that the shape of the cantilever suspension part $6c$ is limited to that suitable for the suspension function and the shapes of the other parts are limited to those suitable for the diaphragm. To this end, as shown in FIGS. 4(*a*) and 4(*b*), the rising part $6b$ is formed at the outer periphery of the pressure receiving surface part $6d$ and ribs $6g$ highly resistant against vibrations along an amplitude direction are integrally formed in the pressure receiving surface part 6d. For the purpose of drawing simplicity, corrugations are not drawn in FIG. 4(a).

INDUSTRIAL APPLICABILITY

According to the invention, the cantilever suspension parts of the diaphragm are formed through laser trimming of the slits. Since the width of the slit is very narrow, a reduction in the pressure receiving surface area of the diaphragm is small so that a large pressure receiving surface area can be obtained. The narrow width of the slit can eliminate the factors of suppressing vibrations of the diaphragm to be caused by sounds, i.e., air pressure reaching the inner surface of the diaphragm. Namely, since the width of the slit is narrow, the viscosity of air increases so that air rarely reaches the inner surface of the diaphragm.

The amplitude of the diaphragm was measured by applying a sound pressure of 94 dB at a frequency of 1 KHz. The amplitude was 1 μm to 2.2 μm. This amplitude corresponds to an increase by about 12.5 times to 27.5 times that of a conventional diaphragm without slits. The amplitude of the diaphragm of this invention has a very high amplitude. The diaphragm having a high performance and being suitable for mass production can be provided for a light sound converter for detecting a vibration displacement of the diaphragm by utilizing light.

The rising part at the periphery of the reflective part provides the effect of a rib so that a fine deformation of the reflective part can be prevented and the sound quality can be prevented from being degraded. As in the second and third embodiments, the cantilever suspension parts 15 are integrally formed to have a height different from that of the nearby parts and slits are formed. As shown in the partial cross sectional views of FIGS. 3(b) and 4(b), the rising part or falling part is formed at the whole outer periphery of the diaphragm. The outer periphery of the diaphragm provides therefore the effects of a rib so that the diaphragm has a reinforced structure. Since the strain is reduced while the diaphragm vibrates, the sound quality can be improved.

This structure is further improved by limiting the shape of the cantilever suspension part 6c to that suitable for the suspension function and by limiting the shapes of the other parts to those suitable for the diaphragm. The slits are formed in this three-dimensional integral structure. As shown in FIG. 4(b), the diaphragm can be formed which has the rising parts 6b at the outer periphery of the pressure receiving surface part 6d and has the ribs 6g highly resistant against vibrations along an amplitude direction. The mechanical strength of the diaphragm and the effective pressure receiving surface area of the diaphragm can therefore be increased. Since the mechanical strength is high and the pressure receiving surface area is increased, it is possible to obtain the diaphragm of a high performance which provides a high sound quality and is likely to increase the vibration amplitude.

According to the invention, since the diaphragm is formed with the slits by laser trimming, the width of the slit can be made very narrow and the width of the cantilever suspension part can be made as narrow as possible to such an extent that the material strength is endurable. It is therefore unnecessary to consider the mechanical strength of the width defined by trimming molds, a punch and a die, as in the conventional case.

Although almost all the area of a conventional diaphragm is removed by press trimming, according to the invention the diaphragm structure having the cantilever suspension parts supporting the diaphragm and having a desired compliance can be obtained without scarcely changing the diaphragm area, i.e., without hardly changing the pressure receiving surface area of the diaphragm.

It is well known that a desired shape can be obtained easily by laser trimming using a program. A desired shape of the cantilever suspension part can therefore be formed. An elasticity of the suspension part can be set as desired and the generation of a resonance can be controlled by defining the shape of the cantilever suspension parts by a curve, a straight line or a combination of a curve and a straight line.

An elasticity of the suspension part can be set as desired and the generation of a resonance can be controlled also by three-dimensionally molding the cantilever suspension parts and forming a recess, a hole, a corrugation or the like at desired positions. With these methods, the suspension characteristics of the cantilever suspension parts supporting the pressure receiving surface part can be controlled as desired.

What is claimed is:

1. An acoustic-electrical converter comprising:
    a diaphragm comprising an integral structure of a light reflective part (1a) at a central area thereof, suspension part (1c, 1d) surrounding the light reflective part, and margin part (1f) surrounding the suspension part and fixed to a frame (2 or 9); and
    a light emitting element (3) and a light receiving element (4) disposed at positions opposed to the light reflective part so that a displacement of said diaphragm is detected by receiving light emitted from said light emitting element and then reflected from the light reflective part at said light receiving element;
    wherein a first slit is formed from a first outer periphery point of the suspension part to a first inner point near the light reflective part,
    wherein a second slit is formed from a second outer periphery point of the suspension part, which is apart from said first outer periphery point by a predetermined width, to a second inner point near the light reflective part so that an area of the suspension part between said first and second slits constitutes a first cantilever suspension (1c) which supports the light reflective part with connecting the light reflective part to the margin part (1f),
    wherein a third slit is formed from a third outer periphery point of the suspension part to a third inner point near the light reflective part,
    wherein a fourth slit is formed from a fourth outer periphery point of the suspension part, which is apart from said third outer periphery point by a predetermined width, to a fourth inner point near the light reflective part so that an area of the suspension part between said third and fourth slits constitutes a second cantilever suspension (1c) which supports the light reflective part with connecting the light reflective part to the margin part (1f),
    wherein an outer slit is formed between the second and third outer periphery points along the outer periphery of said suspension part and an area of the suspension part between the second and third slits constitutes a pressure receiving surface (1d) which is connected to the light reflective part 1a through a portion between the second and third inner points but free of the margin part (1f).

2. An acoustic-electrical converter according to claim 1 further comprising:
    a fifth slit is formed from a fifth outer periphery point of the suspension part to a fifth inner point near the light reflective part,
    a sixth slit is formed from a sixth outer periphery point of the suspension part, which is apart from said fifth outer periphery point by a predetermined width, to a sixth inner point near the light reflective part so that an area of the suspension part between said fifth and sixth slits constitutes a third cantilever suspension (1*c*) which supports the light reflective part with connecting the light reflective part to the margin part (1*f*), a second outer slit is formed between the fourth and fifth outer periphery points along the outer periphery of said suspension part and an area of the suspension part between the fourth and fifth slits constitutes a second pressure receiving surface (1*d*) which is connected to the light reflective part (1*a*) but free of the margin part (1*f*), a third outer slit is formed between the sixth and first outer periphery points along the outer periphery of said suspension part and an area of the suspension part between the sixth and first slits constitutes a third pressure receiving surface (1*d*) which is connected to the light reflective part (1*a*) but free of the margin part (1*f*).

3. An acoustic-electrical converter according to claim 1, wherein a width of each of said slits is 0.1 mm or narrower.

4. An acoustic-electrical converter according to claim 1 wherein said slits are formed by laser trimming.

5. An acoustic-electrical converter according to claim 2, wherein a width of the cantilever suspension part changes from a continuous couple part with the reflective part toward an outer periphery of said diaphragm.

6. An acoustic-electrical converter according to claim 2, wherein each of said slits defining an outer periphery of each of the cantilever suspension parts is made of a predetermined curve, a predetermined straight line or a combination of predetermined curve and straight line.

7. An acoustic-electrical converter according to claim 2, wherein a recess or a hole is formed in a predetermined area of each of the cantilever suspension parts.

8. An acoustic-electrical converter according to claim 2, wherein a corrugation is formed in a predetermined area of each of the cantilever suspension parts.

9. An acoustic-electrical converter according to claim 2, wherein a rising part is formed at an outer periphery of the pressure receiving surface part.

10. An acoustic-electrical converter according to claim 2, wherein a rising part is integrally formed at an outer periphery of each of the cantilever suspension parts of said diaphragm.

11. An acoustic-electrical converter according to claim 2, wherein a rising part is integrally formed at an outer periphery of the reflective part of said diaphragm.

12. An acoustic-electrical converter according to claim 2, wherein a rib is integrally formed at a desired position of the pressure receiving surface part.

* * * * *